(12) United States Patent
Kim

(10) Patent No.: US 12,299,778 B2
(45) Date of Patent: May 13, 2025

(54) METHOD AND APPARATUS FOR GENERATING X-RAY IMAGE AND COMPUTER-READABLE RECORDING MEDIUM

(71) Applicant: OSSTEMIMPLANT CO., LTD., Seoul (KR)

(72) Inventor: Sun Jung Kim, Seoul (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 762 days.

(21) Appl. No.: 17/279,019

(22) PCT Filed: Jul. 17, 2019

(86) PCT No.: PCT/KR2019/008828
§ 371 (c)(1),
(2) Date: Mar. 23, 2021

(87) PCT Pub. No.: WO2020/067636
PCT Pub. Date: Apr. 2, 2020

(65) Prior Publication Data
US 2022/0101570 A1    Mar. 31, 2022

(30) Foreign Application Priority Data

Sep. 27, 2018  (KR) .................. 10-2018-0114696

(51) Int. Cl.
*G06T 7/80* (2017.01)
*G06T 7/73* (2017.01)
*G06T 11/00* (2006.01)

(52) U.S. Cl.
CPC .............. *G06T 11/005* (2013.01); *G06T 7/73* (2017.01); *G06T 2207/10081* (2013.01); *G06T 2207/10116* (2013.01); *G06T 2207/30201* (2013.01)

(58) Field of Classification Search
None
See application file for complete search history.

(56) References Cited

U.S. PATENT DOCUMENTS

| 2014/0107473 | A1* | 4/2014 | Dumoulin | .......... A61B 17/1703 606/130 |
| 2019/0216410 | A1* | 7/2019 | Bae | .......................... A61B 6/00 |
| 2020/0008761 | A1* | 1/2020 | Yoshimura | ............... A61B 6/04 |

FOREIGN PATENT DOCUMENTS

| EP | 3135201 A1 | 3/2017 |
| EP | 3155969 A1 | 4/2017 |

(Continued)

OTHER PUBLICATIONS

Chowdhury et al., "Wide Baseline Image Registration With Application to 3-D Face Modeling," IEEE Transactions on Multimedia, vol. 6, No. 3 (Year: 2004).*

*Primary Examiner* — Vincent Rudolph
*Assistant Examiner* — Nicholas Crespo Stazer
(74) *Attorney, Agent, or Firm* — Bridgeway IP Law Group, PLLC; Sang Ho Lee; Hyun Woo Shin

(57) ABSTRACT

Provided is a method and an apparatus for generating an X-ray. The method for generating an X-ray image by the apparatus includes: obtaining a first camera image of the examinee's head by the camera image obtaining processor; obtaining a first projection image by photographing a first region of the examinee's head by the X-ray photographing unit; changing a relative position between the examinee's head and the X-ray photographing unit by the driving unit; obtaining a second camera image of the examinee's head by the camera image obtaining processor; obtaining a second projection image by photographing a second region of the examinee's head by the X-ray photographing unit; and generating the X-ray image by stitching and reconstructing the first projection image and the second projection image (Continued)

based on the first camera image and the second camera image by the X-ray image generation unit.

19 Claims, 10 Drawing Sheets

(56) References Cited

FOREIGN PATENT DOCUMENTS

| | | | |
|---|---|---|---|
| JP | 2017-063839 A | 4/2017 |
| KR | 10-2017-0081871 A | 7/2017 |
| KR | 10-2017-0116776 A | 10/2017 |
| KR | 10-2018-0027187 A | 3/2018 |
| WO | 2017/117517 A1 | 7/2017 |
| WO | 2018/074854 A1 | 4/2018 |

* cited by examiner

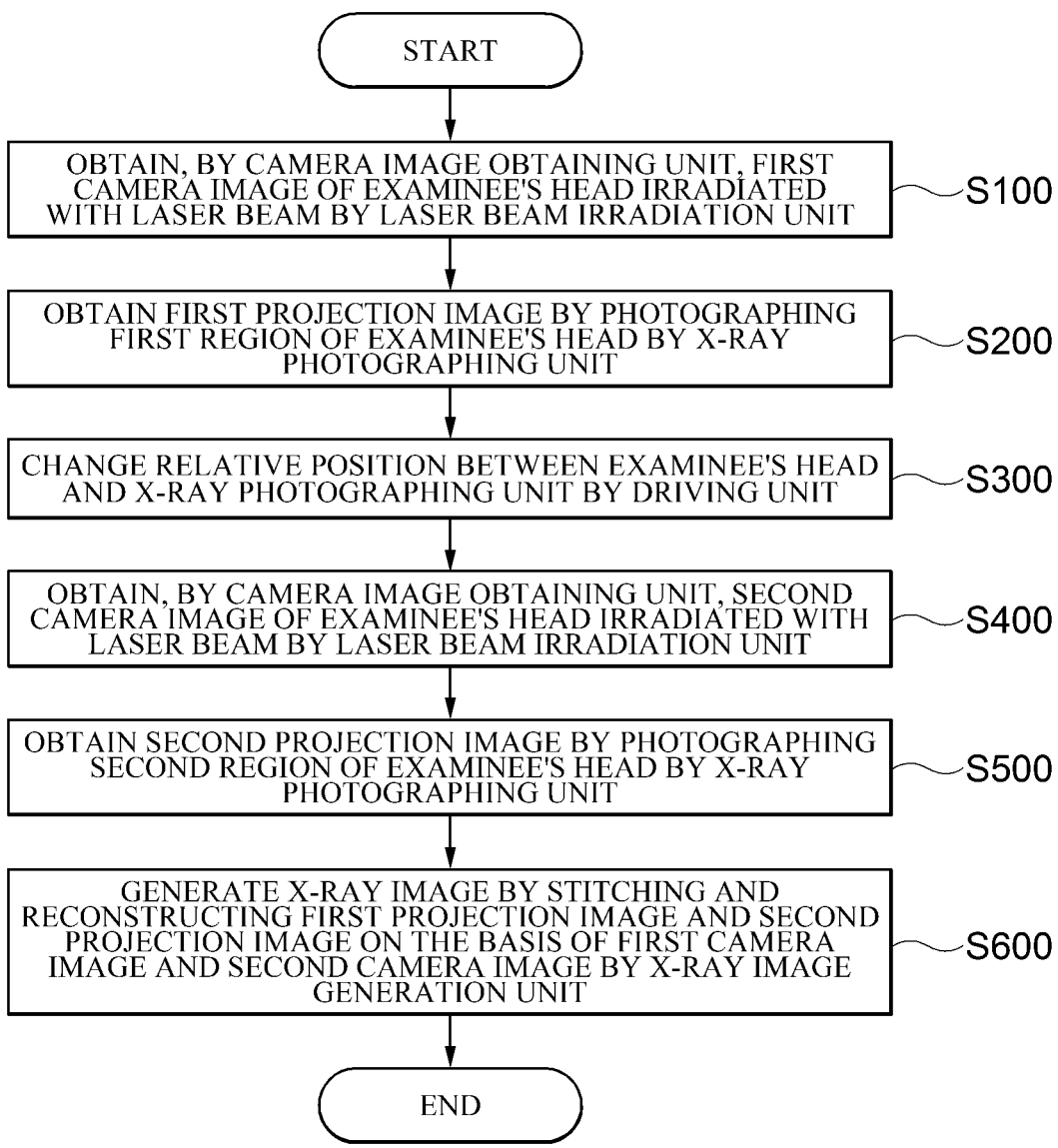

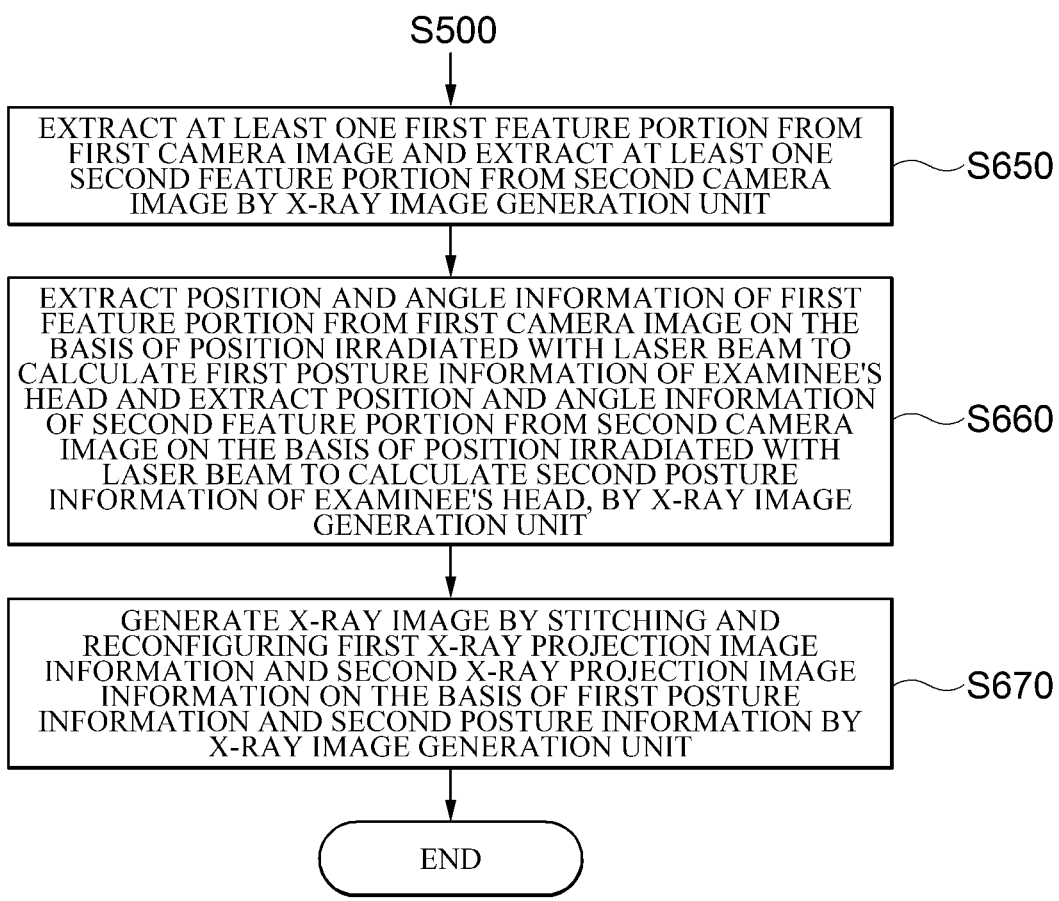

FIG. 9A1
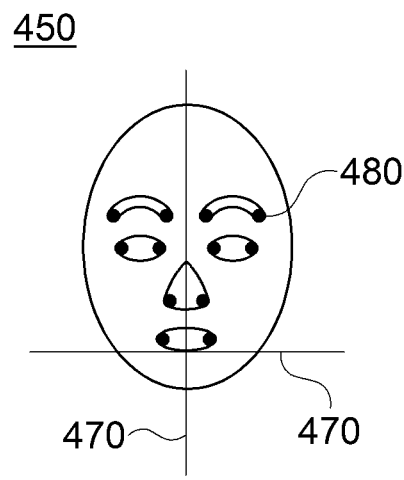
FIG. 9B1
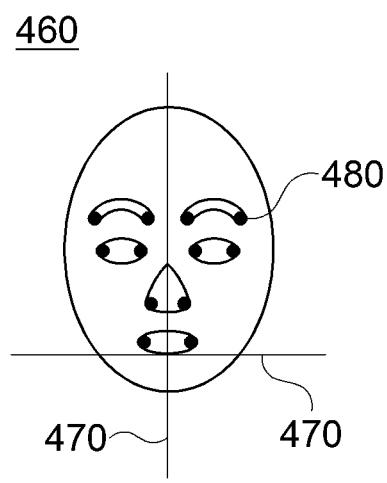

FIG. 9A2
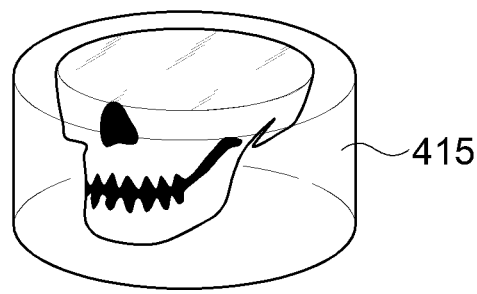
FIG. 9B2
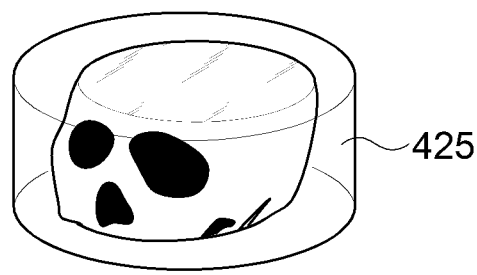
FIG. 9C
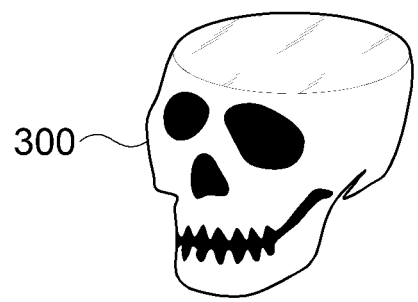

FIG. 10A1
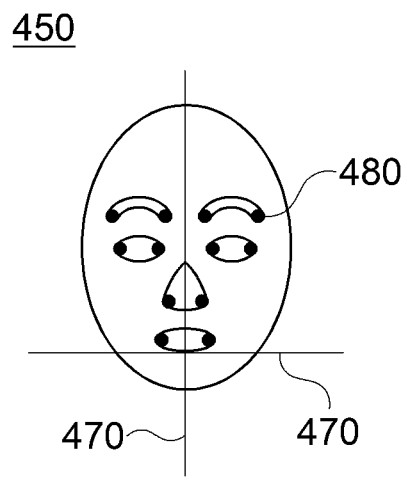
FIG. 10B1
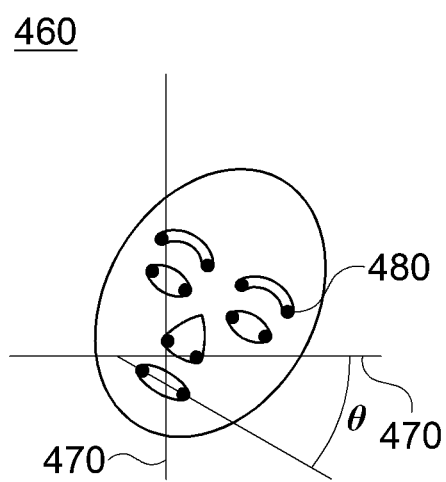

FIG. 10A2
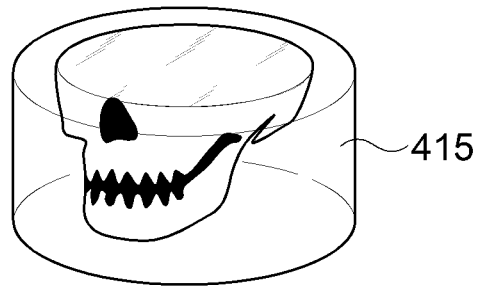
FIG. 10B2
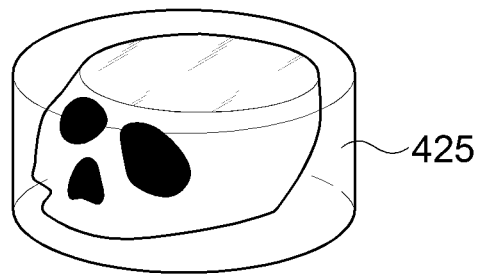
FIG. 10C
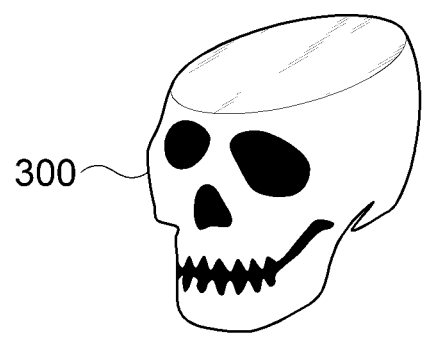

METHOD AND APPARATUS FOR GENERATING X-RAY IMAGE AND COMPUTER-READABLE RECORDING MEDIUM

TECHNICAL FIELD

The present disclosure relates to a method and an apparatus for generating an X-ray image and a computer-readable recording medium.

BACKGROUND ART

X-ray photographing apparatuses widely used in the field of medical technology irradiate a human body with an X-ray and obtain an image inside the human body. Through this, the X-ray photographing apparatuses detect an abnormality inside the human body.

In particular, a panoramic photographing apparatus mainly used in a dental clinic among the X-ray photographing apparatuses may generate images of teeth and an alveolar bone, which are an object of image generation, on one two-dimensional plane, and has thus been usefully used for various diagnostic purposes such as determining of the prognosis of orthodontic treatment, confirming of an eruption station of teeth, and confirming of a height of the alveolar bone.

In addition, a dental computed tomography (CT) photographing apparatus among the X-ray photographing apparatuses is of great help in grasping states of anatomical structures such as a thickness of the alveolar bone and positions of major nerves for implant treatment or the like.

The X-ray photographing apparatus utilized for diagnostic purposes in the dental clinic as described above generally irradiates a body of an examinee with an X-ray generated from a generator, and receives an X-ray that partially passes through or does not pass through the human body of the examinee and arrives at a sensor facing the generator through the sensor. Then, the X-ray photographing apparatus converts the received X-ray converted into an electrical signal to obtain projection data. In particular, such an X-ray photographing apparatus may generate electrical signals required for generating X-ray image data by continuously irradiating the body with X-rays and receiving X-rays while rotating the generator and the sensor around a rotation shaft.

Such a method for obtaining projection data may examine all the states of all teeth and anatomical structures with one-time photographing, and has advantages such as low radiation dose and fast imaging time. The projection data is converted into an X-ray image such as a panoramic image or a CT image through a stitching or reconstruction process. This panoramic image includes all of the images of the anatomical structures including a patient's teeth arrangement on a plane, and thus, is usefully utilized for a dental diagnosis.

Meanwhile, in the dental clinic, an image of a jaw joint or the like, in addition to the teeth arrangement, may be required. That is, if shapes of the teeth arrangement and the jaw joint may be confirmed in one image, this may be of great help in making a comprehensive determination in the dental diagnosis. To this end, there is a need to enlarge an area of the image.

However, the sensor has a limitation in increasing the area in terms of technology or cost. Accordingly, there is a need to propose a configuration of an apparatus and method for generating an X-ray image capable of obtaining an image of a large area even in a case where an area of the sensor is small.

Therefore, a method for generating an X-ray image by photographing a subject a subject (for example, an examinee's head) once, changing a position of the subject, and then photographing the subject again to obtain two image data and combining the two image data with each other may be considered. However, in this case, there is a risk that a posture or a position of the examinee will be changed during a time between first photographing and second photographing. In this case, a high-quality X-ray image may not be expected.

In addition, in order to obtain one X-ray image from two adjacent image data, generally, the image data obtained by the first photographing is subjected to a three-dimensional reconstruction process, and the image data obtained by the second photographing is also subjected to a three-dimensional reconstruction process. The reconstructed images obtained in this manner are stitched into one image. Therefore, there is a problem that a reconstruction time that is two times to third times the reconstruction time in a case of obtaining an X-ray image with only one-time photographing is required.

DISCLOSURE

Technical Problem

The present disclosure has been made in view of the problem described above, and an object of the present disclosure is to provide a method and an apparatus for generating an X-ray image and a computer-readable recording medium capable of confirming shapes of parts necessary for a dental diagnosis in one image through a camera and a sensor of a small area.

Further, another object of the present disclosure is to provide a correction means capable of efficiently correcting and generating an image even though a posture of an examinee is partially changed during photographing.

Further, still another object of the present disclosure is to provide a means capable of reducing a time and resources used for stitching and reconstruction processes for generating an X-ray image.

Technical Solution

According to an aspect of the present disclosure, a method for generating an X-ray image by photographing an examinee's head by an apparatus for generating an X-ray image including an X-ray photographing unit, a driving unit, a stitching display unit, a camera image obtaining unit, and an X-ray image generation unit may include: obtaining, by the camera image obtaining unit, a first camera image of the examinee's head whose stitching is displayed by the stitching display unit; obtaining a first projection image by photographing a first region of the examinee's head by the X-ray photographing unit; changing a relative position between the examinee's head and the X-ray photographing unit by the driving unit after the first region is photographed; obtaining, by the camera image obtaining unit, a second camera image of the examinee's head whose stitching is displayed by the stitching display unit after the relative position is changed; obtaining a second projection image by photographing a second region of the examinee's head by the X-ray photographing unit after the relative position is changed; and generating the X-ray image by stitching and reconstructing the first projection image and the second projection image on the basis of the obtained first camera image and the obtained second camera image by the X-ray image generation unit.

In addition, the X-ray image may be a three-dimensional (3D) computed tomography (CT) image or a panoramic image of the entirety or a part of the examinee's head.

Furthermore, the X-ray image may be a 3D CT image of the entirety or a part of the examinee's head, and the generating of the X-ray image may include: generating a matched projection image by stitching the obtained first projection image and second projection image by the X-ray image generation unit; and generating the X-ray image by reconstructing the matched projection image by the X-ray image generation unit.

Meanwhile, the X-ray image may be a 3D CT image of the entirety or a part of the examinee's head, and the generating of the X-ray image may include: reconstructing each of the first projection image and the second projection image by the X-ray image generation unit; and generating the X-ray image by stitching the reconstructed first projection image and the reconstructed second projection image.

Meanwhile, the generating of the X-ray image may include: extracting at least one first feature portion from the obtained first camera image and extracting at least one second feature portion from the obtained second camera image, by the X-ray image generation unit; extracting position and angle information of the first feature portion from the first camera image on the basis of the stitching to calculate first posture information of the examinee's head and extracting position and angle information of the second feature portion from the second camera image on the basis of the stitching to calculate second posture information of the examinee's head, by the X-ray image generation unit; and generating the X-ray image by stitching and reconfiguring the first X-ray projection image information and the second X-ray projection image information on the basis of the first posture information and the second posture information, by the X-ray image generation unit.

In addition, each of the first feature portion and the second feature portion may include at least one of mark points of images of eyes, eyebrows, a nose, and a mouth.

In addition, in the changing of the relative position between the examinee's head and the X-ray photographing unit by the driving unit, the driving unit may raise or lower the examinee's head in a direction perpendicular to a bottom surface on which the apparatus for generating an X-ray image is installed.

According to another aspect of the present disclosure, an apparatus for generating an X-ray image may include: a stitching display unit displaying a stitching on an examinee's head; a camera image obtaining unit; an X-ray photographing unit; a driving unit; and an X-ray image generation unit, wherein the camera image obtaining unit obtains a first camera image of the examinee's head whose stitching is displayed by the stitching display unit, the X-ray photographing unit obtains a first projection image by photographing a first region of the examinee's head, the driving unit changes a relative position between the examinee's head and the X-ray photographing unit after the first region is photographed, the camera image obtaining unit obtains a second camera image of the examinee's head whose stitching is displayed by the stitching display unit after the relative position is changed, the X-ray photographing unit obtains a second projection image by photographing a second region of the examinee's head after the relative position is changed, and the X-ray image generation unit generates the X-ray image by stitching and reconstructing the first projection image and the second projection image on the basis of the obtained first camera image and the obtained second camera image.

The X-ray image may be a 3D CT image or a panoramic image of the entirety or a part of the examinee's head.

In addition, the X-ray image may be a 3D CT image of the entirety or a part of the examinee's head, and the X-ray image generation unit may generate a matched projection image by stitching the obtained first camera image and the image and then generate the X-ray image by reconstructing the matched projection image.

Meanwhile, the X-ray image may be a 3D CT image of the entirety or a part of the examinee's head, and the X-ray image generation unit may reconstruct each of the first projection image and the second projection image and then generate the X-ray image by stitching the reconstructed first projection image and the reconstructed second projection image.

Meanwhile, the X-ray image generation unit may extract at least one first feature portion from the obtained first camera image and extract at least one second feature portion from the obtained second camera image, extract position and angle information of the first feature portion from the first camera image on the basis of the stitching to calculate first posture information of the examinee's head and extract position and angle information of the second feature portion from the second camera image on the basis of the stitching to calculate second posture information of the examinee's head, and generate the X-ray image by stitching and reconfiguring the first X-ray projection image information and the second X-ray projection image information on the basis of the first posture information and the second posture information.

In addition, each of the first feature portion and the second feature portion may include at least one of mark points of images of eyes, eyebrows, a nose, and a mouth.

The driving unit may raise or lower the examinee's head in a direction perpendicular to a bottom surface on which the apparatus for generating an X-ray image is installed, in order to change the relative position between the examinee's head and the X-ray photographing unit.

In addition, the driving unit may include a chin-nest supporting a jaw of the examinee's head and raise or lower the examinee's head by raising or lowering the chin-nest.

The apparatus may further include a camera photographing the examinee's head, wherein the first camera image and the second camera image are captured by the camera.

The camera image obtaining unit may receive the first camera image and the second camera image transmitted from the outside.

The method for generating an X-ray image described above may be performed by a computer program, and the computer program may be recorded in a computer-readable recording medium.

Advantageous Effects

According to various exemplary embodiments of the present disclosure, shapes of parts necessary for a dental diagnosis may be confirmed in one image through a camera and a sensor of a small area, which may assist in comprehensive determination at the time of the dental diagnosis.

In addition, according to various exemplary embodiments of the present disclosure, even though a posture of an examinee is partially changed during photographing, an image may be efficiently corrected and generated.

Furthermore, according to various exemplary embodiments of the present disclosure, a time and resources used for stitching and reconstruction processes for generating an X-ray image may be reduced.

DESCRIPTION OF DRAWINGS

FIG. 4 is a flowchart for describing a method for generating an X-ray image according to an exemplary embodiment of the present disclosure.

FIG. 8 is a flowchart for describing a method for generating an X-ray image according to an exemplary embodiment of the present disclosure.

FIGS. 9A1 to 9C are schematic views for describing a method for generating an X-ray image according to an exemplary embodiment of the present disclosure.

FIGS. 10A1 to 10C are schematic views for describing a method for generating an X-ray image according to an exemplary embodiment of the present disclosure.

BEST MODE

Figure 1:
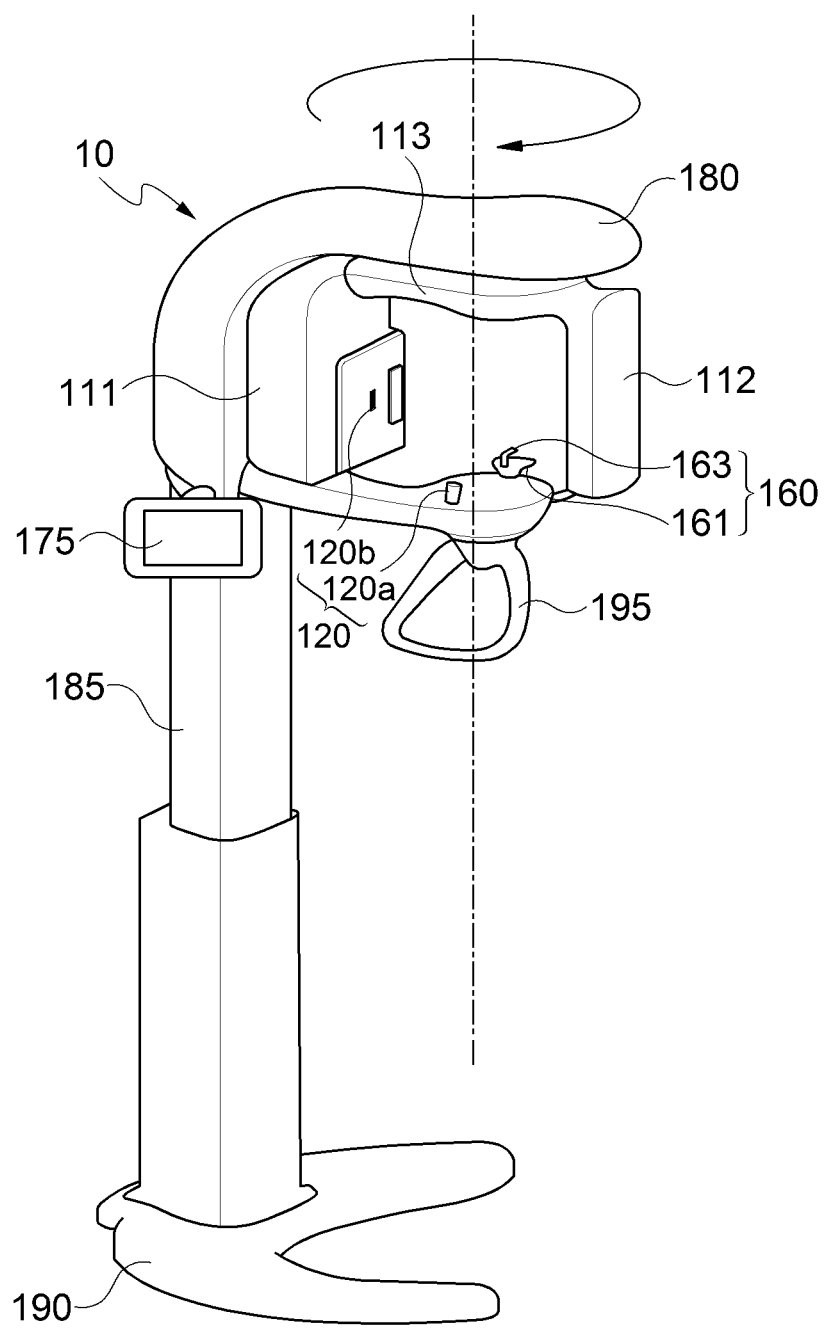
FIG. 1 is an illustrative view illustrating an X-ray photographing apparatus according to the related art.

The following description illustrates only a principle of the present disclosure. Therefore, those skilled in the art may implement the principle of the present disclosure and invent various apparatuses included in the spirit and scope of the present disclosure although not clearly described or illustrated in the present specification. In addition, it is to be understood that all conditional terms and exemplary embodiments mentioned in the present specification are obviously intended only to allow those skilled in the art to understand a concept of the present disclosure in principle, and the present disclosure is not limited to exemplary embodiments and states particularly mentioned as such.

Further, it is to be understood that all detailed descriptions mentioning specific exemplary embodiments of the present disclosure as well as principles, aspects, and exemplary embodiments of the present disclosure are intended to include structural and functional equivalences thereof. Further, it is to be understood that these equivalences include an equivalence that will be developed in the future as well as an equivalence that is currently well-known, that is, all elements invented so as to perform the same function regardless of a structure.

Therefore, it is to be understood that, for example, flowcharts of the present specification illustrate a conceptual aspect of an illustrative circuit for embodying a principle of the present disclosure. Similarly, it is to be understood that all flowcharts, state transition diagrams, pseudo-codes, and the like, illustrate various processes that may be tangibly embodied in a computer-readable medium and that are executed by computers or processors regardless of whether or not the computers or the processors are clearly illustrated.

Functions of various elements including processors or functional blocks represented as concepts similar to the processors and illustrated in the accompanying drawings may be provided using hardware having capability to execute appropriate software as well as dedicated hardware. When the functions are provided by the processors, they may be provided by a single dedicated processor, a single shared processor, or a plurality of individual processors, and some of them may be shared with each other.

In addition, it is to be understood that terms mentioned as a processor, control, or a concept similar to the processor or the control are not interpreted to exclusively cite hardware having capability to execute software, and are implicitly include digital signal processor (DSP) hardware and a read only memory (ROM), a random access memory (RAM), and a non-volatile memory for storing software without being limited thereto. The abovementioned terms may also include well-known other hardware.

In the claims of the present specification, components represented as means for performing functions mentioned in a detailed description are intended to include all methods of performing functions including all types of software including, for example, a combination of circuit elements performing these functions, firmware/micro codes, or the like, and are coupled to appropriate circuits for executing the software so as to execute these functions. It is to be understood that since functions provided by variously mentioned means are combined with each other and are combined with a method demanded by the claims in the present disclosure defined by the claims, any means capable of providing these functions are equivalent to means recognized from the present specification.

The abovementioned objects, features, and advantages will become more obvious from the following detailed description associated with the accompanying drawings. Therefore, those skilled in the art to which the present disclosure pertains may easily practice a technical idea of the present disclosure. Further, in describing the present disclosure, when it is decided that a detailed description of the well-known technology associated with the present disclosure may unnecessarily make the gist of the present disclosure unclear, it will be omitted.

Hereinafter, various exemplary embodiments of the present disclosure will be described in detail with reference to the accompanying drawings.

FIG. 1 is an illustrative view illustrating an X-ray photographing apparatus according to the related art. The X-ray photographing apparatus 10 is an apparatus for photographing an X-ray image 300 including a shape of an anatomical structure of an examinee's body.

The X-ray photographing apparatus 10 may include a pedestal 190, a support pillar 185, a monitor 175, a gantry 113, a knob 195, and a head portion 180.

The pedestal 190 is a component facing a bottom surface on which the X-ray photographing apparatus 10 is installed in order to support standing of the X-ray photographing apparatus 10, and the support pillar 185 stands vertically from the pedestal 190 and has a height that may be adjusted in a sliding manner.

The monitor 175 is a component through which a user may confirm the use of the X-ray photographing apparatus 10 (for example, rotation of the gantry 113, start and end of computed tomography (CT) photographing, or the like). The gantry 113 may be positioned below the head portion 180 of an upper portion of the X-ray photographing apparatus 10.

In addition, an alignment portion 160 may further include at least one of a chin-nest 161 and a bite block 163. As can be seen in FIG. 1, the chin-nest 161 is a component on which a chin of an examinee's head 400 is rested. In addition, the bite block 163 is a component that may be bitten with teeth of the examinee's head 400. A main purpose of the bite block 163 is also to align a posture of the examinee's head 400.

An apparatus 100 for generating an X-ray image according to the present disclosure, which is an apparatus for generating an X-ray image 300 including a shape of an anatomical structure of the examinee's head 400, and may include components of the dental X-ray photographing apparatus 10 illustrated in FIG. 1.

Figure 2:
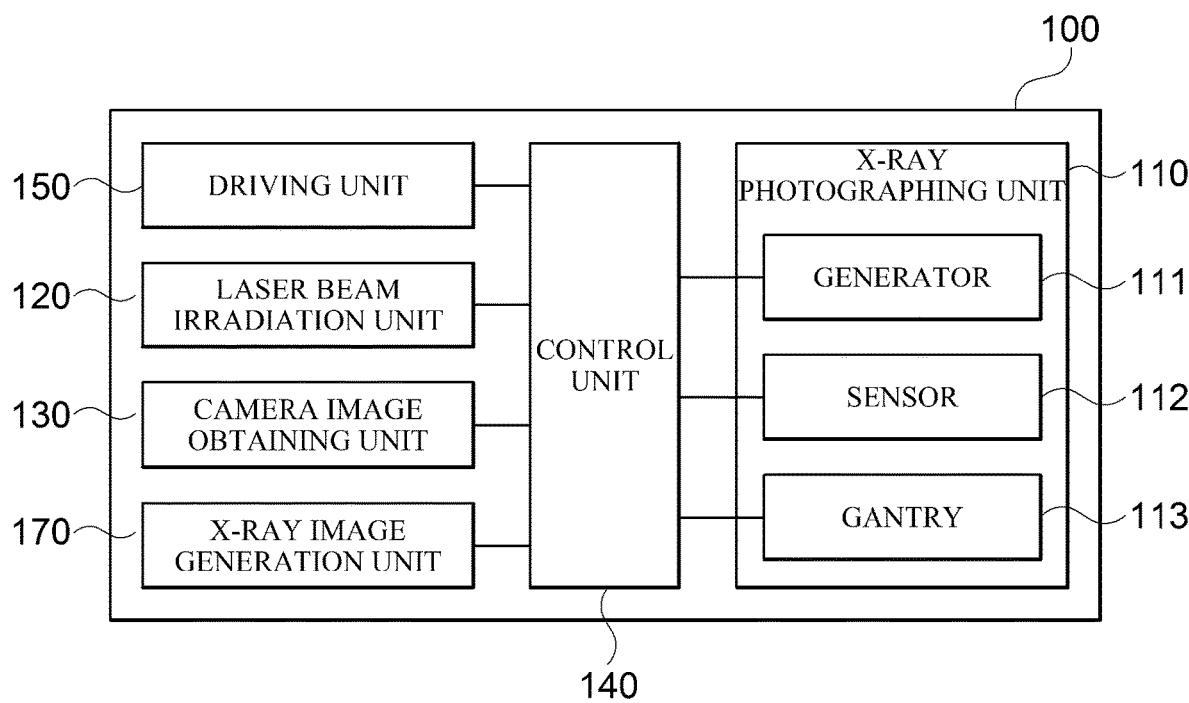
FIG. 2 is a block diagram illustrating components of an apparatus for generating an X-ray image according to an exemplary embodiment of the present disclosure.

FIG. 2 is a block diagram illustrating components of an apparatus for generating an X-ray image according to an exemplary embodiment of the present disclosure.

As illustrated in FIG. 2, the apparatus 100 for generating an X-ray image according to an exemplary embodiment of the present disclosure may basically include an X-ray photographing unit 110, a stitching display unit 120, a camera image obtaining unit 130, a control unit 140, and a driving unit 150.

Furthermore, the apparatus 100 for generating an X-ray image according to an exemplary embodiment of the present disclosure may further include an X-ray image generation unit 170.

According to an exemplary embodiment of the present disclosure, the X-ray photographing unit 110 may include a generator 111, a sensor 112, and a gantry 113.

The generator 111 and the sensor 112 may be attached to both ends of a rotation means called the gantry 113. The gantry 113 may rotate about a rotation shaft (not illustrated) centered on a straight line in a vertical direction of the examinee's head 400.

The driving unit 150, which is a component for changing a relative position between the examinee's head 400 and the X-ray photographing unit 110, may be configured to include a rotary motor, a screw, and a linear guide or may be implemented in a manner including a linear motor.

The relative position may be described as indicating a position of the other of two elements when one of the two elements is used as a reference of a position.

More specifically, the driving unit 150 may include a rotary drive motor (not illustrated), a screw (not illustrated) that rotates by receiving a torque of the drive motor, and a block (not illustrated) that is axially inserted into the screw and moves in a sliding manner along a length direction of the screw by rotation of the screw, and a configuration in which a separate component capable of applying an external force to the examinee's head 400 is attached to the block may be used as a configuration of an exemplary embodiment.

It is preferable that the block is configured to perform a linear motion without departure according to a separately provided linear guide (not illustrated). In addition, it is preferable that stoppers (not illustrated) are provided at both ends of the linear guide or the screw so as to act as limit points of a translational motion.

The driving unit 150 may include the chin-nest 161 as the separate component, and may finally apply an external force to the examinee's head 400 through the chin-nest 161 to adjust a height of the examinee's head 400.

The driving unit 150 may include a chair (not illustrated) on which an examinee (not illustrated) is seated at the time of X-ray photographing as the separate component, and may apply an external force to the examinee (not illustrated) through the chair to adjust the height of the examinee's head 400.

The driving unit 150 may include the support pillar 185 or a rotation shaft (not illustrated) of the gantry 113 as the separate component. In this case, a relative position between the examinee's head 400 and the X-ray photographing unit 110 may be changed while a height of the gantry 113 is adjusted.

The stitching display unit 120 may display a stitching 470 on the examinee's head 400.

In an exemplary embodiment of the present disclosure, the stitching display unit 120 may display the stitching 470 by irradiating the examinee's head 400 with light. More specifically, the stitching display unit 120 may display the stitching 470 by irradiating the examinee's head 400 with a laser beam.

According to an exemplary embodiment of the present disclosure, the stitching display unit 120 may be installed together with an extending arm in which the chin-nest 161 is installed, as a fixed stitching display unit 120a (see FIG. 1).

In addition, according to another exemplary embodiment, the stitching display unit 120 may be installed on the generator 111 movable stitching display unit 120b (see FIG. 1). In a case where the stitching display unit 120 is implemented as a movable stitching display unit 120b, a position of the generator 111 may be aligned with the front of the examinee's head 400 through rotation of the gantry 113 and the stitching 470 may be displayed.

In addition, the apparatus 100 for generating an X-ray image may further include the X-ray image generation unit 170 that obtains a projection image photographed by the X-ray photographing unit 110 to generate the X-ray image 300. The X-ray image generation unit 170 may generate a final X-ray image 300 by performing one or more of the stitching 470 and a reconstruction on the projection data.

In the present disclosure, the stitching 470 may refer to a process of connecting portions where a plurality of images are in contact with each other connected to each other to generate one matched image. In addition, the reconstruction may refer to a process of generating an image through a process of converting image data. The reconstruction and the stitching 470 is a term that refers to a general process used at the time of generating a dental panoramic image or a dental CT image.

Figure 3:
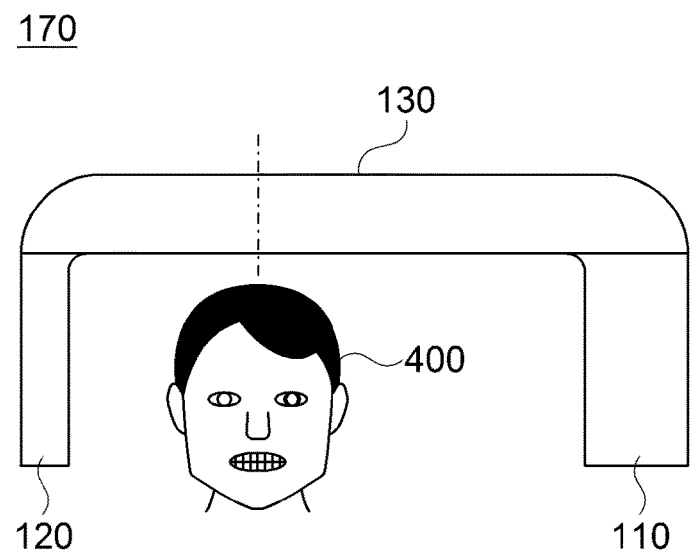
FIG. 3 is an illustrative view illustrating an alignment state of an examinee's head for X-ray photographing in the apparatus for generating an X-ray image according to an exemplary embodiment of the present disclosure.

FIG. 3 is an illustrative view illustrating an alignment state of the examinee's head 400 for X-ray photographing in the apparatus 100 for generating an X-ray image according to an exemplary embodiment of the present disclosure. As illustrated in FIG. 3, the gantry 113, the generator 111, and the sensor 112 may be configured in a 'U' shape, and the examinee's head 400 is positioned and aligned between the gantry 113, the generator 111, and the sensor 112.

Parts mainly handled at the time of a dental diagnosis in the examinee's head 400 include a teeth arrangement and a jaw joint. Therefore, it is preferable that shapes of the teeth arrangement and the jaw joint are included in one X-ray image 300.

However, in a case where the sensor 112 is a small area sensor, it may be difficult to photograph both the shapes of the teeth arrangement 420 and the jaw joint 410 according to one-time rotation of the gantry 113.

FIG. 4 is a flowchart for describing a method for generating an X-ray image according to an exemplary embodiment of the present disclosure. As illustrated in FIG. 4, the method for generating an X-ray image by photographing an examinee's head by the apparatus 100 for generating an X-ray image according to the present disclosure including the X-ray photographing unit 110, the driving unit 150, the stitching display unit 120, the camera image obtaining unit 130, and the X-ray image generation unit 170 may include: obtaining, by the camera image obtaining unit 130, a first camera image 450 of the examinee's head 400 whose stitching 470 is displayed by the stitching display unit 120 (S100); obtaining a first projection image by photographing a first region 410 of the examinee's head 400 by the X-ray photographing unit 110 (S200); changing a relative position between the examinee's head 400 and the X-ray photographing unit 110 by the driving unit 150 (S300) after the first region 410 is photographed; obtaining, by the camera image obtaining unit 130, a second camera image 460 of the examinee's head 400 whose stitching 470 is displayed by the stitching display unit 120 (S400) after the relative position is changed; obtaining a second projection image by photographing a second region 420 of the examinee's head 400 by the X-ray photographing unit 110 after the relative position is changed (S500); and generating the X-ray image 300 by performing the stitching 470 and the reconstruction on the first projection image and the second projection image on the basis of the obtained first camera image 450 and the obtained second camera image 460 by the X-ray image generation unit 170 (S600).

Figure 5A:
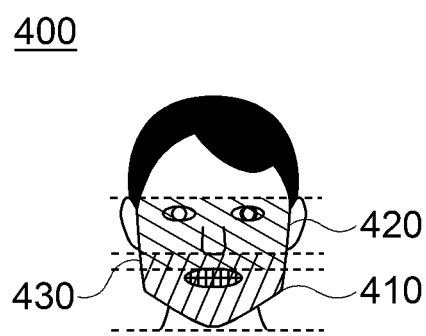
FIGS. 5A and 5B are schematic views for describing a method for generating an X-ray image according to an exemplary embodiment of the present disclosure.
Figure 5B:
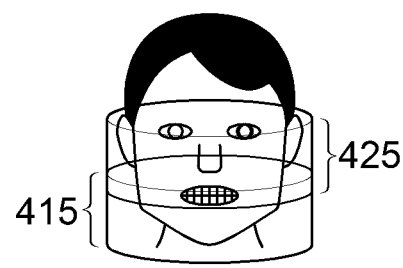

FIGS. 5A and 5B are views for describing a method for generating an X-ray image according to an exemplary embodiment of the present disclosure. As illustrated in FIG. 5A, a region of the examinee's head 400 may be divided into a first region 410 and a second region 420. The first region 410 and the second region 420 may have an overlapping region 430 where they partially overlap each other.

FIG. 5B illustrates a field of view (FOV) of photographing. As illustrated in FIG. 5B, the FOV may be divided into a first FOV 415, which is a photographing region at the time of photographing the first region 410, and a second FOV 425, which is a photographing region at the time of photographing the second region 420.

The FOV refers to a region photographed at the time of X-ray photographing.

It is preferable that the X-ray image 300 is a three-dimensional (3D) CT image or a panoramic image of the entirety or a part of the examinee's head 400.

Figure 6:
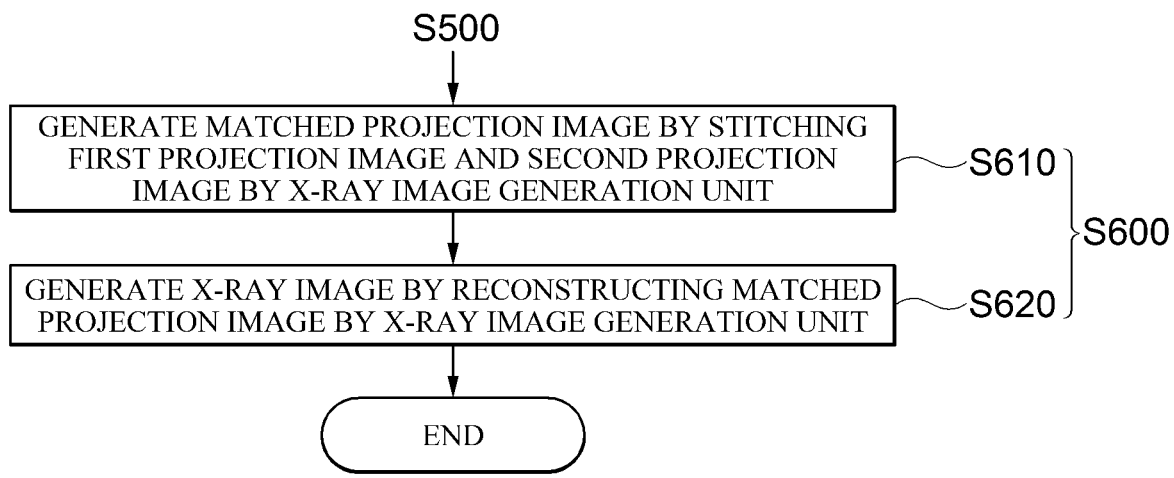
FIG. 6 is a flowchart for describing a method for generating an X-ray image according to an exemplary embodiment of the present disclosure.

FIG. 6 is a flowchart for describing a method for generating an X-ray image according to an exemplary embodiment of the present disclosure.

The X-ray image 300 may be a 3D CT image of the entirety or a part of the examinee's head 400. In this case, as illustrated in FIG. 6, the generating (S600) of the X-ray image 300 may include: generating a matched projection image by stitching the obtained first projection image and second projection image by the X-ray image generation unit 170 (S610); and generating the X-ray image 300 by reconstructing the matched projection image by the X-ray image generation unit 170 (S620).

In order to obtain one X-ray image 300 from two adjacent image data, generally, a three-dimensional reconstruction process is performed on each of image data obtained by first photographing and two-dimensional image data obtained by second photographing, and the respective reconstructed images are then stitched into one image. Therefore, there is a problem that a reconstruction time that is two times to third times the reconstruction time in a case of obtaining the X-ray image 300 with only one-time photographing is required.

In the method for generating an X-ray image according to an exemplary embodiment of the present disclosure, a reconstruction time may be shortened by capturing the first projection image, which is two-dimensional, and the second projection image, which is two-dimensional, so that the first and second projection images partially overlap each other, performing the stitching (S610), and then three-dimensionally reconstructing data over the stitched wide region (S620), as described above.

That is, since a time required for matching two-dimensional data is significantly less than a time required for reconstructing three-dimensional data, it may significantly contribute to reduction of a time and resources for computation to reduce the number of times of the reconstruction as described above.

Figure 7:
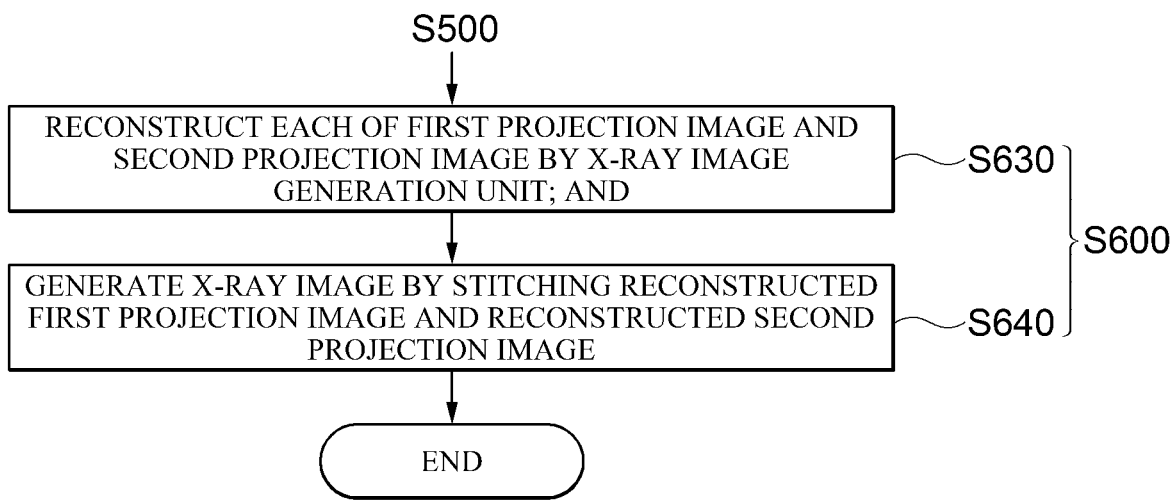
FIG. 7 is a flowchart for describing a method for generating an X-ray image according to an exemplary embodiment of the present disclosure.

FIG. 7 is a flowchart for describing a method for generating an X-ray image according to an exemplary embodiment of the present disclosure. The X-ray image 300 according to an exemplary embodiment of the present disclosure is a three-dimensional CT image of the entirety or a part of the examinee's head 400, and as illustrated in FIG. 7, the method for generating an X-ray image (S600) may include reconstructing each of the first projection image and the second projection image by the X-ray image generation unit 170 (S630); and generating the X-ray image 300 by stitching the reconstructed first projection image and the reconstructed second projection image (S640). That is, the X-ray image 300 may also be obtained by first performing the reconstruction and then performing the stitching.

FIG. 8 is a flowchart for describing a method for generating an X-ray image according to an exemplary embodiment of the present disclosure. As illustrated in FIG. 8, the generating (S600) of the X-ray image 300 may include: extracting at least one first feature portion from the obtained first camera image 450 and extracting at least one second feature portion from the obtained second camera image 460, by the X-ray image generation unit 170 (S650); extracting position and angle information of the first feature portion from the first camera image 450 on the basis of the stitching 470 to calculate first posture information of the examinee's head 400 and extracting position and angle information of the second feature portion from the second camera image 460 on the basis of the stitching 470 to calculate second posture information of the examinee's head 400, by the X-ray image generation unit 170 (S660); and generating the X-ray image 300 by stitching and reconfiguring the first X-ray projection image information and the second X-ray projection image information on the basis of the first posture information and the second posture information (S670).

Each of the first feature portion and the second feature portion may include at least one of mark points 480 of images of eyes, eyebrows, a nose, and a mouth.

This will be described in more detail below with reference to FIGS. 9A1 to 9C and FIGS. 10A1 to 10C.

FIGS. 9A1 to 9C and FIGS. 10A1 to 10C are schematic views for describing a method for generating an X-ray image according to an exemplary embodiment of the present disclosure. In particular, FIGS. 9A1 to 9C illustrate a case where a position or a posture of the examinee's head 400 has not been changed at the time of X-ray photographing of the first region 410 and the X-ray of the second region 420. FIGS. 10A1 to 10C illustrate a case where a position or a posture of the examinee's head 400 has been changed at the time of X-ray photographing of the first region 410 and the X-ray of the second region 420.

FIG. 9A1 and FIG. 10A1 illustrate a first camera image 450, and FIG. 9B1 and FIG. 10B1 illustrate a second camera image 460.

As illustrated in FIGS. 9A1 to 9C and FIGS. 10A1 to 10C, mark points 480 may be points typifying images of eyes, eyebrows, a nose, and a mouth in the camera images 460.

More specifically, the mark points 480 may be points at both ends of each of the eyes, the eyebrows, the nose, and the mouth. As described above, by using both ends of the eyes, the eyebrows, the nose, and the mouth as the mark points 480 utilized as the first and second feature points, it becomes easier to detect the posture of the examinee's head 400. That is, if both ends corresponding to each other are connected to each other with a straight line, it is easy to obtain information on an angle (θ in FIG. 10B1) with respect to the stitching 470.

The first FOV 415 and the second FOV 425 according to the present disclosure may partially overlap each other in a horizontal direction. Such an overlapping region may be a region corresponding to 30 to 50% of each of the first FOV 415 and the second FOV 425. Such an overlapping region may be more preferably a region corresponding to 40% of each of the first FOV 415 and the second FOV 425.

The second camera image 460 illustrated in FIG. 9B1 does not have a difference in posture and position from the second camera image 460 illustrated in FIG. 9A1. In this case, an X-ray image 300 as illustrated in FIG. 9C may be generated by stitching and reconstructing a first projection image of FIG. 9A2 and a second projection image of FIG. 9B2.

FIGS. 9A2, 9B2, 10A2, and 10B2 do not reflect shapes of projection images before being reconstructed. In fact, partial shapes of skeletons illustrated in FIGS. 9A2, 9B2, 10A2, and 10B2 represent reconstructed projection images. In order to assist in understanding the concept, FIGS. 9A2, 9B2, 10A2, and 10B2 illustrate projection images in a reconstructed state.

Meanwhile, in the second camera image 460 illustrated in FIG. 10B1, a shape of the examinee's head 400 is inclined as compared with the second camera image 460 illustrated in FIG. 10A1.

Such a change in position and posture may be derived from corresponding angle and position information in the first feature portion and the second feature portion. That is, the position and angle information of the first feature portion may be extracted to obtain the first posture information of the examinee's head 400, and the position and angle information of the second feature portion may be extracted from the second camera image 460 on the basis of the stitching 470 to obtain the second posture information of the examinee's head 400 (S660).

The first posture information and the second posture information may be expressed as angle and displacement information of the entirety of the examinee's head 400. In addition, the angle and displacement information may include three-dimensional coordinates and angle information.

A movement degree of the examinee's head 400 may be grasped from a difference between the first posture information and the second posture information. As described above, by correcting the position and the posture of at least one of the first and second projection data on the basis of the first posture information and the second posture information and stitching and reconstructing the first and second projection data, it is possible to generate an X-ray image 300 having a high quality as illustrated in FIG. 10C.

In addition, as described above, by obtaining the first posture information and the second posture information from the stitching and the position information of the first feature portion and the second feature portion and correcting the position and posture information of the first and second projection data from the first posture information and the second posture information, a method for generating an image in which the stitching of the projection data is first performed to generate the matched projection data and the reconstruction is later performed may be implemented. In this case, as described above, it is possible to significantly reduce the computational speed as compared with a manner of restructuring and then stitching each projection data.

In the changing of the relative position between the examinee's head 400 and the X-ray photographing unit 110 by the driving unit 150, it is preferable that the driving unit 150 raises or lowers the examinee's head 400 in a direction perpendicular to a bottom surface on which the apparatus for generating an X-ray image is installed.

The apparatus 100 for generating an X-ray image according to the present disclosure may include: a stitching display unit 120 displaying a stitching 470 on an examinee's head; a camera image obtaining unit 130; an X-ray photographing unit 110; a driving unit 150; and an X-ray image generation unit 170, wherein the camera image obtaining unit 130 obtains a first camera image 450 of the examinee's head 400 whose stitching 470 is displayed by the stitching display unit 120, the X-ray photographing unit 110 obtains a first projection image by photographing a first region 410 of the examinee's head 400, the driving unit 150 changes a relative position between the examinee's head 400 and the X-ray photographing unit 110 after the first region 410 is photographed, the camera image obtaining unit 130 obtains a second camera image 460 of the examinee's head 400 whose stitching 470 is displayed by the stitching display unit 120 after the relative position is changed, the X-ray photographing unit 110 obtains a second projection image by photographing a second region 420 of the examinee's head 400 after the relative position is changed, and the X-ray image generation unit 170 generates the X-ray image 300 by stitching and reconstructing the first projection image and the second projection image on the basis of the obtained first camera image 450 and the obtained second camera image 460.

The X-ray image 300 may be a 3D CT image or a panoramic image of the entirety or a part of the examinee's head 400.

In addition, the X-ray image 300 may be a 3D CT image of the entirety or a part of the examinee's head 400, and the X-ray image generation unit 170 may generate a matched projection image by stitching the obtained first camera image 450 and the second camera image 460 and then generate the X-ray image 300 by reconstructing the matched projection image.

Meanwhile, the X-ray image 300 may be a three-dimensional CT image of the entirety or a part of the examinee's head 400, and the X-ray image generation unit 170 may reconstruct each of the first projection image and the second projection image and then generate the X-ray image 300 by stitching the reconstructed first projection image and the reconstructed second projection image.

Meanwhile, the X-ray image generation unit 170 may extract at least one first feature portion from the obtained first camera image 450 and extract at least one second feature portion from the obtained second camera image 460, extract position and angle information of the first feature portion from the first camera image 450 on the basis of the stitching 470 to calculate first posture information of the examinee's head 400 and extract position and angle information of the second feature portion from the second camera image 460 on the basis of the stitching 470 to calculate second posture information of the examinee's head 400, and generate the X-ray image 300 by stitching and reconfiguring the first X-ray projection image information and the second X-ray projection image information on the basis of the first posture information and the second posture information.

In addition, each of the first feature portion and the second feature portion may include at least one of mark points 480 of images of eyes, eyebrows, a nose, and a mouth.

It is preferable that the driving unit 150 raises or lowers the examinee's head 400 in a direction perpendicular to a bottom surface on which the apparatus for generating an X-ray image is installed, in order to change the relative position between the examinee's head 400 and the X-ray photographing unit 110.

In addition, it is preferable that the driving unit 150 includes a chin-nest 161 supporting a jaw of the examinee's head 400 and raises or lowers the examinee's head 400 by raising or lowering the chin-nest 161.

The apparatus 100 for generating an X-ray image further includes a camera (not illustrated) photographing the examinee's head 400, and it is preferable that the first camera image 450 and the second camera image 460 are captured by the camera (not illustrated).

In this case, it is preferable that the camera (not illustrated) is fixed at a position close to the stitching display unit 120.

The camera image obtaining unit 130 may receive the first camera image 450 and the second camera image 460 transmitted from the outside. A wireless transmission manner such as wireless fidelity (Wi-Fi) or Bluetooth may be used.

That is, it is possible to receive a captured camera image transmitted from an external device such as a camera or a smartphone. Even though a user holds the external device with his/her hand and photographs the examinee's head 400, the stitching 470 is displayed on the captured camera image, and it is thus possible to extract the first posture information and the second posture information.

Alternatively, the external device may be fixedly installed on an indoor wall or the like.

In this case, the external device and the apparatus 100 for generating an X-ray image may constitute one system (not illustrated) for generating an X-ray image.

Meanwhile, a computer program for performing the method for generating an X-ray image described above may be stored in a computer-readable recording medium.

That is, the methods for generating an X-ray image according to various exemplary embodiments of the present disclosure described above may be implemented as a computer program and provided to a server or devices in a state in which they are stored in various computer-readable recording media.

The recording medium may be a non-transitory computer readable medium, and the non-transitory computer readable medium is not a medium that stores data for a while, such as a register, a cache, or a memory, but refers to a medium that semi-permanently stores data and is readable by a device. In detail, the various applications or programs described above may be stored and provided in the non-transitory computer readable medium such as a compact disk (CD), a digital versatile disk (DVD), a hard disk, a Blu-ray disk, a universal serial bus (USB), a memory card, a read only memory (ROM), or the like.

In addition, although the exemplary embodiments of the present disclosure have been illustrated and described hereinabove, the present disclosure is not limited to the above-mentioned specific exemplary embodiments, but may be variously modified by those skilled in the art to which the present disclosure pertains without departing from the scope and spirit of the present disclosure as disclosed in the accompanying claims. These modifications should also be understood to fall within the scope of the present disclosure.

The invention claimed is:

1. A method for generating an X-ray image including an X-ray photographing processor, a driving processor, a stitching display processor, a camera image obtaining processor, and an X-ray image generation processor, the method comprising:
   obtaining, by the camera image obtaining processor, a first camera image of an examinee's head,
      wherein the X-ray generation processor measures first angle information and first position information of the first camera image based on a stitching line displayed on the examinee's head and generates first posture information, and
      wherein the first posture information includes first displacement information and first angle data of an entirety of the examinee's head;
   obtaining a first projection image by photographing a first region of the examinee's head by the X-ray photographing processor;
   changing a relative position between the examinee's head and the X-ray photographing processor by the driving processor after the first region is photographed;
   obtaining, by the camera image obtaining processor, a second camera image of the examinee's head after the relative position is changed,
      wherein the X-ray image generation processor measures second angle information and second position information of the second camera image based on the stitching line displayed on the examinee's head and generates second posture information, and
      wherein the second posture information includes second displacement information and second angle data of an entirety of the examinee's head, and
      wherein the first and the second angle data, and the first and the second displacement information include three-dimensional coordinates data;
   obtaining a second projection image by photographing a second region of the examinee's head by the X-ray photographing processor after the relative position is changed;
   correcting at least one of:
      the first position information and the first posture information of the first projection image, and
      the second position information and the second posture information of the second projection image, wherein the correcting is made based on the first posture information and the second posture information; and
   generating the X-ray image by stitching and reconstructing the first projection image and the second projection image based on the first camera image and the second camera image by the X-ray image generation processor,
      wherein the first angle information and the second angle information are measured between the stitching line and a straight line connecting mark points of either eyes, eyebrows, nose, and mouth of the examinee's head for each of the first camera image and the second camera image.

2. The method of claim 1, wherein the X-ray image is a three-dimensional (3D) computed tomography (CT) image or a panoramic image of the entirety or a part of the examinee's head.

3. The method of claim 2, wherein the X-ray image is the 3D CT image of the entirety or the part of the examinee's head, and the generating of the X-ray image includes:
generating a matched projection image by stitching the first projection image and the second projection image by the X-ray image generation processor; and
generating the X-ray image by reconstructing the matched projection image by the X-ray image generation processor.

4. The method of claim 2, wherein the X-ray image is the 3D CT image of the entirety or the part of the examinee's head, and
the generating of the X-ray image includes:
reconstructing each of the first projection image and the second projection image by the X-ray image generation processor; and
generating the X-ray image by stitching a reconstructed first projection image and a reconstructed second projection image.

5. The method of claim 1, wherein each of first feature portion and second feature portion includes at least one of mark points of images of the eyes, the eyebrows, the nose, and the mouth.

6. The method of claim 1, wherein in the changing of the relative position between the examinee's head and the X-ray photographing processor by the driving processor,
the driving processor raises or lowers the examinee's head in a direction perpendicular to a bottom surface on which an apparatus for generating the X-ray image is installed.

7. The method of claim 1, wherein the stitching line is displayed in a perpendicular cross-shaped on the examinee's head.

8. The method of claim 1, wherein a generator and a sensor are attached to both ends of a gantry of the X-ray photographing processor, and wherein the gantry rotates around an axis positioned along with a vertical direction of the examinee's head.

9. An apparatus for generating an X-ray image, comprising:
a stitching display processor displaying a stitching on an examinee's head;
a camera image obtaining processor, wherein the camera image obtaining processor is configured to obtain a first projection image by photographing a first region of the examinee's head, and a second projection image by photographing a second region of the examinee's head after a relative position is changed;
an X-ray photographing processor;
a driving processor, wherein the driving processor is configured to change the relative position between the examinee's head and the X-ray photographing processor; and
an X-ray image generation processor, wherein the camera image obtaining processor obtains a first camera image and a second camera image of the examinee's head,
wherein the X-ray generation processor is configured to measure first angle information and first position information of the first camera image based on a stitching line displayed on the examinee's head and generate first posture information,
wherein the first posture information includes first displacement information and first angle data of an entirety of the examinee's head,
wherein the X-ray image generation processor is configured to measure second angle information and second position information of the second camera image based on the stitching line displayed on the examinee's head and generate second posture information, and
wherein the second posture information includes second displacement information and second angle data of an entirety of the examinee's head, and
wherein the X-ray image generation processor is configured to correct at least one of:
the first position information and the first posture information of the first projection image, and
the second position information and the second posture information of the second projection image, wherein the correcting is made based on the first posture information and the second posture information,
wherein the first and the second angle data, and the first and the second displacement information include three-dimensional coordinates data,
and
wherein the X-ray image generation processor generates the X-ray image by stitching and reconstructing the first projection image and the second projection image based on the first camera image and the second camera image,
wherein the first angle information and the second angle information are measured between the stitching line and a straight line connecting mark points of either eyes, eyebrows, nose, and mouth of the examinee's head for each of the first camera image and the second camera image.

10. The apparatus of claim 9, wherein the X-ray image is a 3D CT image or a panoramic image of the entirety or a part of the examinee's head.

11. The apparatus of claim 10, wherein the X-ray image is the 3D CT image of the entirety or the part of the examinee's head, and
the X-ray image generation processor generates a matched projection image by stitching the first camera image and the second camera image and then generates the X-ray image by reconstructing the matched projection image.

12. The apparatus of claim 10, wherein the X-ray image is the 3D CT image of the entirety or the part of the examinee's head, and
the X-ray image generation processor
reconstructs each of the first projection image and the second projection image and then generates the X-ray image by stitching a reconstructed first projection image and a reconstructed second projection image.

13. The apparatus of claim 9, wherein the X-ray image generation processor extracts at least one first feature portion from the first camera image and extracts at least one second feature portion from the second camera image,
extracts the first position information and the first angle information of the first feature portion from the first camera image based on the stitching line to calculate the first posture information of the examinee's head and extracts the second position information and the second angle information of the second feature portion from the second camera image based the stitching to calculate the second posture information of the examinee's head, and
generates the X-ray image by stitching and reconfiguring the first X-ray projection image information and the second X-ray projection image information based on the first posture information and the second posture information.

14. The apparatus of claim 13, wherein each of the first feature portion and the second feature portion includes at least one of mark points of images of the eyes, the eyebrows, the nose, and the mouth.

15. The apparatus of claim 9, wherein the driving processor raises or lowers the examinee's head in a direction perpendicular to a bottom surface on which the apparatus for generating an X-ray image is installed, and change the relative position between the examinee's head and the X-ray photographing processor.

16. The apparatus of claim 15, wherein the driving processor includes a chin-nest supporting a jaw of the examinee's head and raises or lowers the examinee's head by raising or lowering the chin-nest.

17. The apparatus of claim 9, further comprising
a camera photographing the examinee's head,
wherein the first camera image and the second camera image are captured by a camera.

18. The apparatus of claim 9, wherein the camera image obtaining processor receives the first camera image and the second camera image transmitted from the outside.

19. A non-transitory computer-readable recording medium in which a computer program for performing a method for generating an X-ray image is recorded, the method comprising:
obtaining, by a camera image obtaining processor, a first camera image of an examinee's head,
wherein a X-ray generation processor measures first angle information and first position information of the first camera image based on a stitching line displayed on the examinee's head and generates first posture information, and
wherein the first posture information includes first displacement information and first angle data of an entirety of the examinee's head;
obtaining a first projection image by photographing a first region of the examinee's head by a X-ray photographing processor;
changing a relative position between the examinee's head and the X-ray photographing processor by a driving processor after the first region is photographed;
obtaining, by the camera image obtaining processor, a second camera image of the examinee's head after the relative position is changed,
wherein the X-ray image generation processor measures second angle information and second position information of the second camera image based on the stitching line displayed on the examinee's head and generates second posture information, and
wherein the second posture information includes second displacement information and second angle data of an entirety of the examinee's head, and
wherein the first and the second angle data, and the first and the second displacement information include three-dimensional coordinates data;
obtaining a second projection image by photographing a second region of the examinee's head by the X-ray photographing processor after the relative position is changed;
correcting at least one of:
the first position information and the first posture information of the first projection image, and
the second position information and the second posture information of the second projection image, wherein the correcting is made based on the first posture information and the second posture information; and
generating the X-ray image by stitching and reconstructing the first projection image and the second projection image based on the first camera image and the second camera image by the X-ray image generation processor,
wherein the first angle information and the second angle information are measured between the stitching line and a straight line connecting mark points of either eyes, eyebrows, nose, and mouth of the examinee's head for each of the first camera image and the second camera image.

* * * * *